US008236760B2

(12) United States Patent
Pimentel et al.

(10) Patent No.: US 8,236,760 B2
(45) Date of Patent: Aug. 7, 2012

(54) USE OF GLP-1 RECEPTOR AGONISTS FOR THE TREATMENT OF SHORT BOWEL SYNDROME

(75) Inventors: Mark Pimentel, Los Angeles, CA (US); Edy E. Soffer, Los Angeles, CA (US); Jeffrey Conklin, Los Angeles, CA (US)

(73) Assignee: Cedars-Sinsai Medical Center, Los Angeles, CA (US)

( * ) Notice: Subject to any disclaimer, the term of this patent is extended or adjusted under 35 U.S.C. 154(b) by 0 days.

(21) Appl. No.: 12/597,892

(22) PCT Filed: Apr. 24, 2008

(86) PCT No.: PCT/US2008/061417
§ 371 (c)(1),
(2), (4) Date: Nov. 4, 2009

(87) PCT Pub. No.: WO2008/134425
PCT Pub. Date: Nov. 6, 2008

(65) Prior Publication Data
US 2010/0137212 A1    Jun. 3, 2010

Related U.S. Application Data

(60) Provisional application No. 60/914,687, filed on Apr. 27, 2007, provisional application No. 60/915,901, filed on May 3, 2007.

(51) Int. Cl.
*A61K 38/26* (2006.01)
*A61K 38/00* (2006.01)
(52) U.S. Cl. ......................... 514/7.2; 514/11.7; 530/300
(58) Field of Classification Search ......................... None
See application file for complete search history.

(56) References Cited

U.S. PATENT DOCUMENTS

| 5,424,286 A * | 6/1995 | Eng ................................. 514/5.9 |
| 6,348,447 B1 | 2/2002 | Hellstrom et al. |
| 6,858,576 B1 | 2/2005 | Young et al. |
| 2003/0017440 A1 * | 1/2003 | Bergey et al. ................. 434/262 |
| 2006/0293232 A1 * | 12/2006 | Levy et al. ....................... 514/12 |

FOREIGN PATENT DOCUMENTS

WO    2008/134425 A1    6/2008

OTHER PUBLICATIONS

Drucker, Gut 50: 428-435, 2002.*
Jeppesen et al., Gut 54: 1224-1231, 2005.*
Naslund et al., Am. J. Physiol. 277: 46: R910-R916, 1999.*
Barksdale et al., Current Gastr. Reports, 4: 229-237, 2002.*
Anvari et al. Local, exendin -(9-39)-insensitive, site of action of GLP-1 in canine ileum. American Journal of Physiology Gastrointestinal and Liver Physiology (2002) 283:G595-G602.
Naslund et al. Glucagon-like-peptide-1 analogue LY315902: Effect on intestinal motility and release of insulin and somatostatin. Regulatory Peptides (2002) 106:89-95.
Schirra et al. The physiological role of GLP-1 in human: Incretin, ileal brake or more? Regulatory Peptides (2005) 128:109-115.
PCT/US2008/061417 IPRP dated Oct. 27, 2009.
PCT/US2008/061417 Written Opinion dated Aug. 28, 2008.
Kunkel et al. Efficiency of the glucagon-like peptide-1 agonist exenatide in the treatment of short bowel syndrome. Neurogastroenterol Motil (2011); pp. 1-7.
Sleisenger et al. "Gastroenterology and Hepatology" Ed. Mark Feldman, Lawrence S. Friedmank, Lawrence J. Brandt (2010). Chapter on Short Bowel Syndrome by Alan L. Bachman, p. 1794.
Thompson et al. Current management of the Short Bowel Syndrome. Sur Clin N. Am (2011) 91: pp. 493-510.

* cited by examiner

*Primary Examiner* — Gyan Chandra
(74) *Attorney, Agent, or Firm* — Linda B. Huber, Esq.; Nixon Peabody LLP

(57) ABSTRACT

The present invention describes the methods of using incretin mimetics such as GLP-1 receptor agonists, particularly exenatide, to treat short bowel syndrome and spastic or hyperactive esophageal motor disorders.

17 Claims, No Drawings ically referenced is prior art.
USE OF GLP-1 RECEPTOR AGONISTS FOR THE TREATMENT OF SHORT BOWEL SYNDROME This application is the National Phase of International Application PCT/US08/61417, filed Apr. 24, 2008, which designated the U.S. and that International Application was published under PCT Article 21(2) in English. This application also includes a claim of priority under 35 U.S.C. §119(e) to U.S. provisional patent application No. 60/914,687, filed Apr. 27, 2007, and U.S. provisional patent application No. 60/915,901, filed May 3, 2007.

FIELD OF INVENTION

This invention relates to the use of GLP-1 receptor agonists to treat short bowel syndrome and spastic or hyperactive esophageal motor disorders.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

One gastrointestinal disorder is short bowel syndrome (SBS), also referred to as small intestine insufficiency. SBS is a serious, often life-threatening, medical problem resulting in severe diarrhea and nutritional deprivation. Injury or trauma may cause short bowel syndrome; for example, surgical removal of a large portion of the small intestine. The removal may result in the lack of surface area in the remaining bowel to absorb enough nutrients from food. Short bowel syndrome may also be caused by the small intestine's loss of absorptive function due to diseases; for example, Crohn's disease and cancer. Though rare, short bowel syndrome may be congenital and is often referred to as Congenital Short Bowel Syndrome.

Other symptoms of short bowel syndrome include, but are not limited to abdominal pain, steatorrhoea, greasy stools, edema, weight loss, and fatigue. The symptoms result from a lack of absorptive surface and loss of the braking mechanisms controlling the proximal gut. One of the missing, distally produced, peptides that control the proximal gut is glucagon-like peptide-1 (GLP-1). Complications due to short bowel syndrome include weight loss, malnutrition, weakened bones, gallstones, bacterial overgrowth, metabolic acidosis and kidney stones.

Currently available treatments for short bowel syndrome aim to relieve its symptoms. A high-calorie and low-residue diet may be prescribed. Medications attempt to lengthen the time the nutrients are available in the intestine for absorption. In instances wherein normal feeding is not delivering enough nutrients, parenteral nutrition may be necessary. Surgery, such as intestinal lengthening or tapering, may be performed.

Currently, there is no cure for short bowel syndrome and treatment options are not completely effective for all patients. Thus, there is a need in the art for alternative or improved methods and compositions to treat short bowel syndrome.

Other gastrointestinal disorders include spastic or hyperactive esophageal motor disorders which may limit the delivery of food and liquid, as well as cause painful symptoms. Examples of spastic or hyperactive esophageal motor disorders include, but are not limited to, esophageal spasms, nutcracker esophagus and achalasia.

Esophageal spasms are uncoordinated series of muscle contractions that prevent the proper traveling of food into the stomach. Some signs and symptoms of esophageal spasms include chest pain, difficulty swallowing, painful swallowing, a sensation that an object is stuck in the throat, regurgitation, and heartburn. Short term treatment of esophageal spasms may involve the use of medications to relax the esophageal muscles. Long term treatment of esophageal spasms may include management of any contributing health condition (e.g., gastroesophageal reflux disease ("GERD")), medications, and alteration of eating habits.

Nutcracker esophagus is an abnormality wherein swallowing contractions are too powerful. Symptoms of nutcracker esophagus include chest pain, dsyphagia, and heartburn. Treatment options for nutcracker esophagus include anti-reflux therapy to treat an underlying cause (e.g., GERD), use of medications such as nitrates or calcium channel blockers to relax the esophageal and stomach muscles, and use of tricyclic antidepressants to lower the pain sensation.

Achalasia is an esophageal disorder wherein the esophagus is less able to move food towards the stomach and the muscle from the esophagus to the stomach does not relax as much as it needs to be during swallowing. Symptoms of achalasia include difficulty swallowing liquids and solids, regurgitation of food, chest pain, weight loss, heart burn and cough. Current treatment for achalasia seeks to reduce the pressure at the lower esophageal sphincter; for example, widening of the lower esophageal sphincter or injecting the lower esophageal sphincter with botulimun toxin to paralyze it and prevent spasms. Long-acting nitrates and calcium channel blockers may also be used to lower the pressure of the lower esophageal sphincter. Complications of achalasia may include perforation of the esophagus, reflux, and aspiration of food into the lungs.

However, anti-reflux medications only reduce a risk factor for these conditions; medications to relax the muscles only provide relief to some patients and their effectiveness overall is not very good; and the use of antidepressants only treats the associated pain, rather than the abnormalities themselves. Thus, there exists a need in the art for alternative and/or additional treatments for spastic or hyperactive esophageal motor disorders.

SUMMARY OF THE INVENTION

The following embodiments and aspects thereof are described and illustrated in conjunction with compositions and methods which are meant to be exemplary and illustrative, not limiting in scope.

The present invention provides a method for treating a gastrointestinal disorder in a subject in need thereof, comprising: providing an incretin mimetic; and administering a therapeutically effective amount of the incretin mimetic to the subject. In one embodiment, the incretin mimetic may be a glucagon-like peptide-1 (GLP-1) receptor agonist. In a particular embodiment, the GLP-1 receptor agonist may be an exendin. Particularly useful exendins may include exendin-3, exendin-4, and functional derivatives thereof. One particularly useful exendin may be exenatide. GLP-1 receptor agonists that may also be used include GLP-1 and biologically active forms of GLP-1. In other embodiments, the GLP-1 receptor agonist may be a purified polypeptide having an amino acid sequence at least 95% identical to SEQ ID NO: 1. In still other embodiments, the GLP-1 receptor agonist may be a purified polypeptide as disclosed by SEQ ID NO: 1 with up to five conservative amino acid substitutions.

In various embodiments, the gastrointestinal disorder treated may be selected from the group consisting of short bowel syndrome, spastic or hyperactive esophageal motor disorder, and combinations thereof. In particular embodiments, the spastic or hyperactive esophageal motor disorder treated may be selected from the group consisting of esophageal spasm, nutcracker esophagus, achalasia and combinations thereof. In one particular embodiment, the gastrointestinal disorder treated may be short bowel syndrome.

In various embodiments, the therapeutically effective amount administered may be about 5 micrograms (mcg) to about 10 mcg. Administering may comprise administering the therapeutically effective amount twice per day.

The present invention also provides a method of normalizing bowel function in a subject in need thereof, comprising: providing an incretin mimetic; and administering a therapeutically effective amount of the incretin mimetic to the subject. Normalizing bowel function may comprise reducing the number of bowel movements in the subject. The incretin mimetic may be a GLP-1 receptor agonist, as noted above. Further, the GLP-1 receptor agonists may be as described herein. The therapeutically effective amount administered may also be about 5 micrograms (mcg) to about 10 mcg. Further, administering may also comprise administering the therapeutically effective amount twice per day.

The present invention also provides for a kit for treating a gastrointestinal disorder in a subject in need thereof, comprising: an incretin mimetic; and instructions to administer a therapeutically effective amount of the incretin mimetic to the subject. The incretin mimetic may be a GLP-1 receptor agonist as noted above and described herein. The gastrointestinal disorder treated by the kit may be selected from the group consisting of short bowel syndrome, spastic or hyperactive esophageal motor disorder and combinations thereof. Instructions may include instructions to administer a therapeutically effective amount of an incretin mimetic, and particularly, a GLP-1 receptor agonist described herein twice per day.

Other features and advantages of the invention will become apparent from the following detailed description, which illustrate, by way of example, various features of embodiments of the invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); and March, *Advanced Organic Chemistry Reactions, Mechanisms and Structure* 5$^{th}$ ed., J. Wiley & Sons (New York, N.Y. 2001) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, lessening or alleviating symptoms or complications associated with the disease condition, preventing the disease condition from worsening, curing the disease condition and prolonging a patient's life or life expectancy.

"Conditions" and "disease conditions" as used herein may include, but are in no way limited to any form of short bowel syndrome and spastic or hyperactive esophageal motor disorders such as esophageal spasms, nutcracker esophagus and achalasia.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating" as used herein refer to both therapeutic treatment and prophylactic or preventative measures, wherein the object is to prevent, reduce the occurrences or lessen the symptoms associated with the targeted condition or disease condition even if the treatment is ultimately unsuccessful. Those in need of treatment include those already with the condition or disease condition as well as those prone to have the condition or disease condition or those in whom the condition or disease condition is to be prevented.

Short Bowel Syndrome

The present invention is based upon the inventors' discovery that glucagon-like peptide-1 (GLP-1) receptor agonists are useful for the treatment of short bowel syndrome. In various embodiments, GLP-1 receptor agonists may be synthetic or natural exendins such as exendin-3 (HSDGTFTSDLSKQMEEEAVRLFIEWLKNGGPSSGAPPPS; SEQ ID NO: 2), or exendin-4 (HGEGTFTSDLSKQMEEEAVRLFIEWLKNGGPSSGAPPPS; SEQ ID NO 3); insulinotropic fragments of exendin-4 comprising the amino acid sequences: exendin-4(1-31) (HGEGTFTSDLSKQMEEEAVRLFIEWLKNGGP; SEQ ID NO: 4) or exendin-4(1-31) (HGEGTFTSDLSKQMEEEAVRLFIEWLKNGGY; SEQ ID NO: 5); or functional derivatives thereof as described in U.S. Pat. No. 5,424,286, herein incorporated by reference as though fully set forth in its entirety. The '286 Patent also describes additional GLP-1 receptor agonists that may be appropriate for use in accordance with various embodiments of the present invention. Additional GLP-1 receptor agonists and/or exendins and exendin variants that may be appropriate for use with various embodiments of the present invention include those described by U.S. Pat. Nos. 6,858,576, 6,872,700, 6,902,744, 6,956,026, 7,297,761 herein incorporated by reference as though fully set forth in their entirety. One particularly useful GLP-1 receptor agonist is exenatide. Exenatide (BYETTA®) is currently marketed by Amylin Pharmaceuticals, Inc. and Eli Lilly and Company as adjunctive therapy to improve glycemic control in patients with type 2 diabetes mellitus.

In various embodiments, methods of treating short bowel syndrome in a subject in need thereof are provided. One method comprises providing a GLP-1 receptor agonist and administering a therapeutically effective amount of the GLP-1 receptor agonist to the subject in need of treatment for short bowel syndrome. The method may further comprise identifying a subject in need of treatment for short bowel syndrome. The identification may be made by any individual, for example, a medical practitioner or the subject himself. In a particular embodiment, the GLP-1 receptor agonist is exenatide (e.g., BYETTA® exenatide injection).

Exenatide is a synthetic 39-amino acid peptide amide. Exenatide has the empirical formula $C_{184}H_{252}N_{50}O_{60}S$ and molecular weight of 4186.6 Daltons. The amino acid sequence for exenatide is as follows: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$. (SEQ ID NO: 1).

Exenatide belongs to a class of drugs referred to as incretin mimetics. Thus, another method comprises providing an incretin mimetic and administering a therapeutically effective amount of the incretin mimetic to a subject in need of treatment for short bowel syndrome. The method may further comprise identifying a subject in need of treatment for short bowel syndrome.

In an alternative embodiment, a naturally produced GLP-1 hormone or a biologically active forms of GLP-1, such as GLP-1-(7-37) and GLP-1-(7-36)$NH_2$, may be used to treat short bowel syndrome. The method may comprise providing a purified quantity of GLP-1 or a biologically active form of GLP-1 and administering a therapeutically effective amount of the GLP-1 or the biologically active form of the GLP-1 to a subject with short bowel syndrome to treat the short bowel syndrome.

In another alternate embodiment, a purified polypeptide comprising SEQ ID NO: 1 may be used to treat short bowel syndrome. Additionally, a purified polypeptide comprising 38, 37, 36, or 35 consecutive residues of SEQ ID NO: 1 may be used to treat short bowel syndrome. Further, a purified polypeptide with an amino acid sequence comprising a sequence at least 80%, 85%, 90%, 95%, 96%, 97%, 98% or 99% identical to SEQ ID NO: 1 may be used to treat short bowel syndrome.

In a further embodiment, a purified polypeptide comprising the amino acid sequence of SEQ ID NO: 1 but with one, two, three, four or five conservative amino acid substitutions may be used to treat short bowel syndrome. A conservative amino acid substitution as used herein refers to a replacement of an amino acid residue with a different residue having similar physicochemical characteristics; for example, size, charge and polarity or nonpolarity.

The present invention also provides methods of normalizing bowel function in a subject in need thereof. For example, the GLP-1 receptor agonists or the incretin mimetics described above may be used to reduce the number of bowel movements in the subject.

Spastic or Hyperactive Esophageal Motor Disorders

The present invention is also based upon the inventors' discovery that GLP-1 receptor agonists are useful for the treatment of spastic or hyperactive esophageal motor disorders. Similar to the treatment of short bowel syndrome, in various embodiments, GLP-1 receptor agonists used to treat spastic or hyperactive esophageal motor disorders may be exendins or exendin derivatives as described above. One particularly useful GLP-1 receptor agonist is exenatide.

The inventors found that treatment with exenatide reduces esophageal contraction amplitudes. While not wishing to be bound by any particular theory, the inventors believe that the reduction in contraction amplitudes is effective for treating spastic or hyperactive esophageal motor disorders.

In various embodiments, methods of treating a spastic or hyperactive esophageal motor disorder in a subject in need thereof are provided. One method comprises providing a GLP-1 receptor agonist and administering a therapeutically effective amount of the GLP-1 receptor agonist to the subject in need of treatment for a spastic or hyperactive esophageal motor disorder. The method may further comprise identifying a subject in need of treatment for a spastic or hyperactive esophageal motor disorder. In various embodiments, the spastic or hyperactive esophageal motor disorder treated by the inventive method may be esophageal spasms, nutcracker esophagus or achalasia. In a particular embodiment, the GLP-1 receptor agonist used is exenatide Another method comprises providing an incretin mimetic and administering a therapeutically effective amount of the incretin mimetic to a subject in need of treatment for a spastic or hyperactive esophageal motor disorder. The method may also comprise identifying a subject in need of treatment for a spastic or hyperactive esophageal motor disorder. In various embodiments, the spastic or hyperactive esophageal motor disorder treated with the incretin mimetic may be esophageal spasms, nutcracker esophagus or achalasia.

In an alternative embodiment, a naturally produced GLP-1 hormone or a biologically active forms of GLP-1, such as GLP-1-(7-37) and GLP-1-(7-36)$NH_2$, may be used to treat the spastic or hyperactive esophageal motor disorder. The method may comprise providing a purified quantity of GLP-1 or a biologically active form of the GLP-1 and administering a therapeutically effective amount of the GLP-1 or the biologically active form of the GLP-1 to a subject with a spastic or hyperactive esophageal motor disorder to treat the spastic or hyperactive esophageal motor disorder.

In another alternate embodiment, a purified polypeptide comprising SEQ ID NO: 1 may be used to treat a spastic or hyperactive esophageal motor disorder. Additionally, a purified polypeptide comprising 38, 37, 36, or 35 consecutive residues of SEQ ID NO: 1 may be used to treat a spastic or hyperactive esophageal motor disorder in a subject in need thereof. Further, a purified polypeptide with an amino acid sequence comprising a sequence at least 80%, 85%, 90%, 95%, 96%, 97%, 98% or 99% identical to SEQ ID NO: 1 may be used to treat a spastic or hyperactive esophageal motor disorder. In a further embodiment, a purified polypeptide comprising the amino acid sequence of SEQ ID NO: 1, but with one, two, three, four or five conservative amino acid substitutions may be used to treat a spastic or hyperactive esophageal motor disorder in a subject in need thereof.

In another embodiment, the present invention also provides a method of reducing esophageal contraction amplitudes in a subject in need thereof. The method comprises, providing an incretin mimetic or a GLP-1 receptor agonist as described above and administering the incretin mimetic or the GLP-1 receptor agonist to the subject to reduce the esophageal contraction amplitudes.

In other embodiments, the present invention provides pharmaceutical compositions including a pharmaceutically acceptable excipient along with a therapeutically effective amount of a GLP-1 receptor agonist or an incretin mimetic. In a particular embodiment, the GLP-1 receptor agonist or incretin mimetic is exenatide. "Pharmaceutically acceptable excipient" means an excipient that is useful in preparing a pharmaceutical composition that is generally safe, non-toxic, and desirable, and includes excipients that are acceptable for veterinary use, as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, subcutaneous, or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulating, and compressing, when necessary, for tablet forms; or milling, mixing and filling for producing hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Typical dosages of an effective amount of a GLP-1 receptor agonist or an incretin mimetic, particularly exenatide, may be about 5 micrograms (mcg) to 10 mcg and may be given subcutaneously twice per day. Dosages may also be about 10 mcg to about 20 mcg. The dosages may also be given only once per day or more than twice per day. Dosages can also be in the ranges recommended by the manufacturer where known therapeutic compounds are used, and also as indicated to the skilled artisan by the in vitro responses or responses in animal models. Currently, exenatide is marketed as BYETTA® exenatide injection by Amylin Pharmaceuticals. In one embodiment, exenatide may be administered in accordance with the guidelines provided by Amylin Pharmaceuticals for BYETTA® exenatide injection. For example, it may be initiated at 5 mcg per dose and administered twice daily at anytime within a 60 minute period before the morning and evening meals. It may be increased to 10 mcg twice daily after one month of therapy. For further guidance, the full prescribing information for BYETTA® exenatide injection is available from Eli Lilly and Company. While, BYETTA® exenatide injection is administered via injection, other forms of administration as described above are included in the scope of the present invention. Dosages can typically be reduced by up to about one order of magnitude in concentration or amount without losing the relevant biological activity. Thus, the actual dosage may depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to kits to treat short bowel syndrome and/or spastic or hyperactive esophageal motor disorders (e.g., esophageal spasms, nutcracker esophagus and achalasia) in a subject in need thereof. The kit is useful for practicing the inventive method of treating short bowel syndrome and/or spastic or hyperactive esophageal motor disorders. The kits include an assemblage of materials or components, including at least one of the inventive compositions. Thus, in some embodiments the kit contains a composition including a GLP-1 receptor agonist or an incretin mimetic, particularly exenatide, or a polypeptide as described above.

The exact nature of the components configured in the inventive kit depends on its intended purpose. For example, some embodiments are configured for the purpose of treating short bowel syndrome in a subject in need thereof. In other embodiments, the kit is configured for the purpose of treating spastic or hyperactive esophageal motor disorders. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to alleviate symptoms related to short bowel syndrome, to treat short bowel syndrome, to alleviate symptoms related to spastic or hyperactive esophageal motor disorders, or to treat spastic or hyperactive esophageal motor disorders. Optionally, the kit also contains other useful components such as diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in treatment of intestinal diseases or injection-type therapies. As used herein, the term "package" refers to a suitable solid matrix or material such as glass, plastic, paper, foil, and the like, capable of holding the individual kit components. Thus, for example, a package can be a syringe used to contain suitable quantities of an inventive composition containing a GLP-1 receptor agonist, an incretin mimetic or particularly, exenatide. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

A patient was on total parenteral nutrition with only two feet of small bowel. Typically, less than three feet of small bowel is too little to survive on food alone. The patient was having nutritional compromise. He would experience diarrhea within 15 minutes of eating. Normal eating habits resulted in experiencing more than 10 bowel movements a day. Without the i.v. feedings, he would lose ten pounds in one week due to dehydration. In July 2006, the patient was administered Byetta® exenatide and on the same day of administration, he did not experience a bowel movement until six hours after a meal. Since the commencement of treatment with Byetta® exenatide, he has not required i.v. feeding and experiences 1-2 solid bowel movements a day. The patient's bowel health returned to normal and returned to work within one week of starting treatment with Byetta® exenatide. The patient's nutritional status improved dramatically and has normalized. The patient has been using Byetta® exenatide since July 2006.

Example 2

Short bowel syndrome (SBS) subjects were selected based on clinical symptoms and history of greater than 50% distal small bowel resection. Before beginning exenatide treatment, each patient completed a questionnaire documenting stool frequency and consistency. In addition, SBS symptoms, CBC, chemistries and BMI were also obtained. An antroduodenal manometry study was performed during fasting, after exenatide, and after a subsequent test meal. Each patient was then started on exenatide 5 to 10 mcg subcutaneously twice a day. Over the following month the parameters measured at baseline were repeated.

Example 3

The subjects consisted of 4 males and 1 female, ages 46 to 69 (mean: 57.2). At baseline, all patients had severe diarrhea that ranged from 7 to 15 bowel movements per day, often occurring within 15 minutes of eating. After exenatide treatment, all 5 patients had an immediate improvement in bowel frequency and form. In the most severely affected patient, the bowel movements reduced from 15 watery bowel movements per day to 2-3 formed stool. In all subjects, bowel movements were no longer meal related and often occurred hours after any meal. At baseline nutritional parameters were stable due to total parenteral nutrition (TPN) in most cases (n=3). However, after exenatide treatment, all 3 patients no longer needed TPN. Despite the lack of TPN, no weight loss or biochemical nutritional deterioration was observed in any case. Previous attempts at ceasing TPN had resulted in immediate and life-threatening dehydraton and malnutrition. Using normal bowel function as a goal, subjects described their improvement with exenatide treatment as 65-100% improved. Antroduodenal manometry in 2 out of 5 subjects demonstrated continuous low amplitude gastric contractions during fasting which completely normalized after exenatide.

Example 4

A patient was administered Byetta® exenatide. A catheter was placed in the esophagus and esophageal contraction amplitudes were reduced.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for treating short bowel syndrome in a subject in need thereof, comprising:
   providing a composition comprising exendin-4 (SEQ ID NO:3), a fragment of exendin-4 having the sequence disclosed by SEQ ID NO: 4, a fragment of exendin-4 having the sequence disclosed by SEQ ID NO: 5, exenatide (SEQ ID NO: 1), or combinations thereof, and a pharmaceutically acceptable excipient or carrier; and
   administering a therapeutically effective amount of the composition to the subject to treat the short bowel syndrome.

2. The method of claim 1, wherein the composition comprises exenatide and the pharmaceutically acceptable excipient or carrier.

3. The method of claim 1, wherein the therapeutically effective amount is about 5 micrograms (mcg) to about 10 mcg.

4. The method of claim 1, wherein administering comprises administering the therapeutically effective amount twice per day.

5. The method of claim 1, wherein the composition comprises exendin-4 (SEQ ID NO:3) and the pharmaceutically acceptable excipient or carrier.

6. The method of claim 1, wherein the composition comprises the fragment of exendin-4 having the sequence disclosed by SEQ ID NO: 4 and the pharmaceutically acceptable excipient or carrier.

7. The method of claim 1, wherein the composition comprises the fragment of exendin-4 having the sequence disclosed by SEQ ID NO: 5 and the pharmaceutically acceptable excipient or carrier.

8. The method of claim 1, wherein the composition comprises a combination of the exendin-4 (SEQ ID NO:3), fragment of exendin-4 having the sequence disclosed by SEQ ID NO: 4, fragment of exendin-4 having the sequence disclosed by SEQ ID NO: 5, and exenatide (SEQ ID NO: 1), and the pharmaceutically acceptable excipient or carrier.

9. A method of normalizing bowel function in a subject having short bowel syndrome in need thereof, comprising:
   providing a composition comprising an exendin-4 (SEQ ID NO:3), a fragment of exendin-4 having the sequence disclosed by SEQ ID NO: 4, a fragment of exendin-4 having the sequence disclosed by SEQ ID NO: 5, exenatide (SEQ ID NO: 1), or combinations thereof, and a pharmaceutically acceptable excipient or carrier; and
   administering a therapeutically effective amount of the composition to the subject to normalize bowel function.

10. The method of claim 9, wherein normalizing bowel function comprises reducing the number of bowel movements in the subject.

11. The method of claim 9, wherein the composition comprises exenatide and the pharmaceutically acceptable excipient or carrier.

12. The method of claim 9, wherein the therapeutically effective amount is about 5 micrograms (mcg) to about 10 mcg.

13. The method of claim 9, wherein administering comprises administering the therapeutically effective amount twice per day.

14. The method of claim 9, wherein the composition comprises exendin-4 (SEQ ID NO:3) and the pharmaceutically acceptable excipient or carrier.

15. The method of claim 9, wherein the composition comprises the fragment of exendin-4 having the sequence disclosed by SEQ ID NO: 4 and the pharmaceutically acceptable excipient or carrier.

16. The method of claim 14, wherein the composition comprises the fragment of exendin-4 having the sequence disclosed by SEQ ID NO: 5 and the pharmaceutically acceptable excipient or carrier.

17. The method of claim 9, wherein the composition comprises a combination of the exendin-4 (SEQ ID NO:3), fragment of exendin-4 having the sequence disclosed by SEQ ID NO: 4, fragment of exendin-4 having the sequence disclosed by SEQ ID NO: 5, and exenatide (SEQ ID NO: 1), and the pharmaceutically acceptable excipient or carrier.

* * * * *

UNITED STATES PATENT AND TRADEMARK OFFICE
CERTIFICATE OF CORRECTION

PATENT NO. : 8,236,760 B2
APPLICATION NO. : 12/597892
DATED : August 7, 2012
INVENTOR(S) : Mark Pimentel et al.

Page 1 of 1

It is certified that error appears in the above-identified patent and that said Letters Patent is hereby corrected as shown below:

On the title page, item (73), "Assignee", the name "Cedars-Sinsai Medical Center" should read
--Cedars-Sinai Medical Center--

Signed and Sealed this
Twenty-fifth Day of March, 2014

Michelle K. Lee
*Deputy Director of the United States Patent and Trademark Office*

SEQUENCE LISTING

```
<160> NUMBER OF SEQ ID NOS: 5

<210> SEQ ID NO 1
<211> LENGTH: 39
<212> TYPE: PRT
<213> ORGANISM: Artificial Sequence
<220> FEATURE:
<223> OTHER INFORMATION: Synthesized Peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma horridum

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma suspectum

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 31
<212> TYPE: PRT
<213> ORGANISM: Heloderma suspectum

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 5
```

```
<211> LENGTH: 31
<212> TYPE: PRT
<213> ORGANISM: Heloderma suspectum

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
            20                  25                  30
```